United States Patent
Marchyn et al.

(10) Patent No.: US 8,216,242 B2
(45) Date of Patent: Jul. 10, 2012

(54) MODULAR PATELLA INSTRUMENT

(75) Inventors: Duane J. Marchyn, Portsmouth, OH (US); Louis M. Starace, Suffern, NY (US); David J. Neal, Oak Ridge, NJ (US); Gennaro Barile, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1342 days.

(21) Appl. No.: 11/635,957

(22) Filed: Dec. 8, 2006

(65) Prior Publication Data

US 2007/0118141 A1 May 24, 2007

(51) Int. Cl.
*A61B 17/17* (2006.01)
*A61B 17/90* (2006.01)

(52) U.S. Cl. .......................................... 606/88; 606/102

(58) Field of Classification Search .................. 606/102, 606/79–85, 86 R, 87–89
See application file for complete search history.

(56) References Cited

U.S. PATENT DOCUMENTS

| | | | |
|---|---|---|---|
| 4,633,862 A | 1/1987 | Petersen | |
| 4,663,862 A | 5/1987 | Gorissen | |
| 4,706,660 A * | 11/1987 | Petersen | 606/86 R |
| 4,721,104 A | 1/1988 | Kaufman et al. | |
| 4,759,350 A | 7/1988 | Dunn et al. | |
| 5,021,055 A | 6/1991 | Burkinshaw et al. | |
| 5,108,401 A | 4/1992 | Insall | |
| 5,129,907 A * | 7/1992 | Heldreth et al. | 606/80 |
| 5,147,365 A | 9/1992 | Whitlock et al. | |
| 5,222,955 A | 6/1993 | Mikhail | |
| 5,284,482 A | 2/1994 | Mikhail | |
| 5,417,695 A | 5/1995 | Axelson, Jr. | |
| 5,441,884 A | 8/1995 | Baum | |
| 5,486,177 A * | 1/1996 | Mumme et al. | 606/79 |
| 5,520,692 A * | 5/1996 | Ferrante | 606/80 |
| 5,536,271 A * | 7/1996 | Daly et al. | 606/80 |
| 5,542,947 A | 8/1996 | Treacy | |
| 5,575,793 A * | 11/1996 | Carls et al. | 606/80 |
| 5,658,291 A * | 8/1997 | Techiera | 606/80 |
| 5,716,362 A | 2/1998 | Treacy | |
| 5,941,884 A * | 8/1999 | Corvelli et al. | 606/88 |
| 6,010,509 A | 1/2000 | Delgado et al. | |
| 6,159,246 A | 12/2000 | Mendes et al. | |

(Continued)

OTHER PUBLICATIONS

Biomet Catalog; Simple Instruments—Surgical Technique for the Knee.

*Primary Examiner* — Thomas C. Barrett
*Assistant Examiner* — Christopher Beccia
(74) *Attorney, Agent, or Firm* — Lerner, David, Littenberg, Krumholz & Mentlik, LLP (57) ABSTRACT

A patella clamp has a first part including a reference surface engageable with the anterior surface of a patella. The first part includes a stop surface spaced from the reference surface. A second clamping part is provided which is moveable with respect to the first clamping part. A cutting element coupled to the first clamping part is moveable with respect to the first part. The cutting element includes a shaft with an adjustable collar mounted on the shaft for movement with respect to the longitudinal axis of the shaft and cutting element. The adjustable collar on the shaft is engageable with a stop surface on the first part for spacing the cutting element a desired distance from the reference surface. A pair of gages are provided for selectively setting the position of the adjustable collar with respect to either the amount of patella bone being removed or the amount of patella bone remaining.

24 Claims, 10 Drawing Sheets

U.S. PATENT DOCUMENTS

| | | |
|---|---|---|
| 6,174,314 B1 | 1/2001 | Waddell |
| 6,277,121 B1 | 8/2001 | Burkinshaw et al. |
| 6,602,258 B1 | 8/2003 | Katz |
| 7,632,279 B2 * | 12/2009 | Bastian .................... 606/88 |
| 2003/0163137 A1 | 8/2003 | Smucker et al. |
| 2003/0171757 A1 | 9/2003 | Coon |

* cited by examiner

FIG. 11

MODULAR PATELLA INSTRUMENT

This application is a divisional of U.S. application Ser. No. 10/366,014, filed on Feb. 13, 2003, the disclosure of which is incorporated herein by reference.

BACKGROUND OF THE INVENTION

A patellar clamp and reamer are used during a total knee arthroplasty procedure to prepare the posterior surface of a patellar bone to accept a prosthetic implant.

Typically, a surgeon will select to install a patellar prosthesis either by utilizing a resurfacing technique wherein the prosthetic patella will be positioned on the prepared surface of the patella or by an insetting technique wherein the prosthetic patella will be recessed or inset into the prepared surface of the patella. Accordingly, two varieties of guides could be available for connection to the patellar clamp and could be interchangeably connectable to the clamp. The interchangeable guides permit a surgeon to use the patellar clamp during either a total patellar bone resurfacing procedure or a patella insetting procedure.

In either a total resurfacing procedure or a patella insetting procedure, it is important that a sufficient amount of bone stock remain after resection to accept the fixation pegs of the patellar prosthesis and maintain the integrity of the remaining patellar bone.

Prior art devices for aiding the surgeon in performing patella resections are well known to those skilled in the art. For example, Peterson, in U.S. Pat. No. 4,663,862, teaches a method and instruments for the installation of a patella button prosthesis which involves performing a patella resection.

In particular, Peterson describes a saw guide which comprises a pliers-like instrument having a pair of mutually pivotable jaw members. The jaw members are designed so as to enable them to surround the outer periphery of the patella with each jaw member having a respective handle, integrally formed therewith, which handles may be pivoted so as to pivot the jaw members to and from engagement with the patella periphery. At the ends of the handles, a locking device is provided which enables the locking of the jaw members about the patella periphery. The Peterson device requires that a flat saw blade be guided over the face of the jaw members after the patella has been set to the correct depth between the members.

U.S. Pat. No. 5,147,365 relates to a patella osteotomy guide in which the jaw members include a slot for guiding the flat saw blade and an arm for setting the saw blade depth in the patella.

Milling instruments are known in the preparation of the femur for a prosthetic implant. One such milling system is disclosed in U.S. Pat. No. 4,721,104 in which the area between the condyles of a femur is shaped. U.S. Pat. No. 5,417,695 shows the use of a milling instrument to prepare the condylar area of a femur prior to receiving an implant.

U.S. Pat. No. 5,486,177 relates to a patella milling instrument having a clamp which contacts the underside of the patella. A similar clamping tool is shown in U.S. Pat. No. 5,284,482.

U.S. Pat. No. 5,222,955 relates to a reaming system designed to cut a conical bore in a patella surface while the patella is being held in a patella clamp similar to that disclosed in U.S. Pat. No. 5,284,482.

U.S. Pat. No. 5,941,884, the teachings of which are incorporated herein by reference, relates to a patella clamp which includes indicia of both the amount of bone resected and the amount of bone remaining. The resection depth is set via a stop collar on a toothed extension. Corvelli et al. does not provide any method of setting the depth of the patella milling based on the amount of bone remaining. U.S. Pat. No. 5,575,793 is similar in that a gage is provided to set the amount of bone to be removed.

SUMMARY OF THE INVENTION

It is an object of the invention to provide an improved apparatus and method for facilitating the preparation of the natural patella to receive a patellar prosthesis.

It is an additional object of the invention to provide a clamping system which can hold the patella in position during resection and which can be set to either resect a predetermined amount of bone from the patella or, alternately, to set the depth of the remaining bone on the patella.

It is an additional object of the invention to provide a clamping system wherein various modular instruments may be easily attached and removed from the gripping portion of the clamping system.

These and other objects and advantages of the invention are provided by a patella clamp which has a first part, including a jaw reference surface engageable with an anterior surface of the patella and includes a stop surface spaced from the patella engaging surface. A second part is moveable with respect to the first part and a cutting element also moveable with respect to first part is provided. The preferred cutting element includes a shaft having an adjustable collar mounted on the shaft for movement with respect to the longitudinal axis of the shaft. The adjustable collar is engageable with the stop surface on the first part for spacing the cutting element a desired distance from the first jaw reference surface. The collar position may be set with at least one gage to limit the movement of the reamer based on either the desired amount of bone remaining or the amount of bone removed. A separate marker is provided for indicating the position of the reamer with respect to either the patella bone remaining or the amount of bone removed.

In a preferred embodiment, two gage elements are provided, one for setting the position of the collar along the shaft with respect to the first jaw patella contacting reference surface based on the amount of bone remaining and one based on the amount of bone removed. The two gage elements may either be independent of the structure of the patella clamp or can be made part of the clamp.

The shaft includes at one end a cutting element such as a reamer or end mill which is used to shape the posterior surface of the patella. At the other end the shaft includes a coupling portion for engaging a rotary tool such as a drill chuck mounted on an electric battery or air powered tool. The shaft has a collar engaging portion with external ratchet like teeth which selectively engage complementary internal teeth on the collar. The teeth on the collar may be moveable into and out of engagement with the teeth on the shaft so that the collar may be easily adjusted axially along the shaft.

The second jaw part also includes a clamping element or jaw which is tubular and has circumferential teeth for engaging the bone of the patella. The cutting element may be cylindrical in shape and extend within the tubular clamping jaw. Thus, the tubular jaw holds the patella in position as the bone removal operation with the cutting element progresses. Cutting of the patella proceeds after the first and second part are locked in position with the patella firmly clamped between the tubular clamping jaw and the patella engaging surface which engages the anterior side of the patella. The cutting element then moves independently of the first and second clamping parts.

The tubular clamping jaw and the opposite engaging surface mounted on the first part are removably attached to the body or frame of the clamp. This permits not only different size clamping parts to be utilized but allows for the use of other cutting tools to be mounted on the clamp.

The shaft has a flange or stop surface for engaging a second or outwardly facing surface of the collar and upon engagement of the collar surface and shaft surface the surface of the collar which contacts the stop surface on the first part is spaced from the reference surface a distance allowing the cutting element base to be positioned adjacent the reference surface engageable with the anterior surface of the patella when the collar and said stop surface contact. Thus, the distance between the flange and corresponding collar surface is identical to the amount of the bone remaining on the patella after the cutter removes bone until the corresponding collar and first part stop surface is engaged. Similarly, the distance between the collar stop surface and the stop surface on the first part equals the amount of bone to be removed.

A pair of gage elements are provided with each gage having a plurality of steps of different height for varying for the bone remaining or bone removing thicknesses for setting the position of the collar along the shaft. The steps can be in 1 millimeter increments with six (6) steps being on each gage element. Obviously, fewer or a greater number of steps may be included. The bone remaining thickness gage is inserted between the stop surface on the collar and the stop surface on the first jaw part and the bone remaining gage would be inserted between the flange on the shaft and the top surface of the collar.

DETAILED DESCRIPTION

Figure 1:
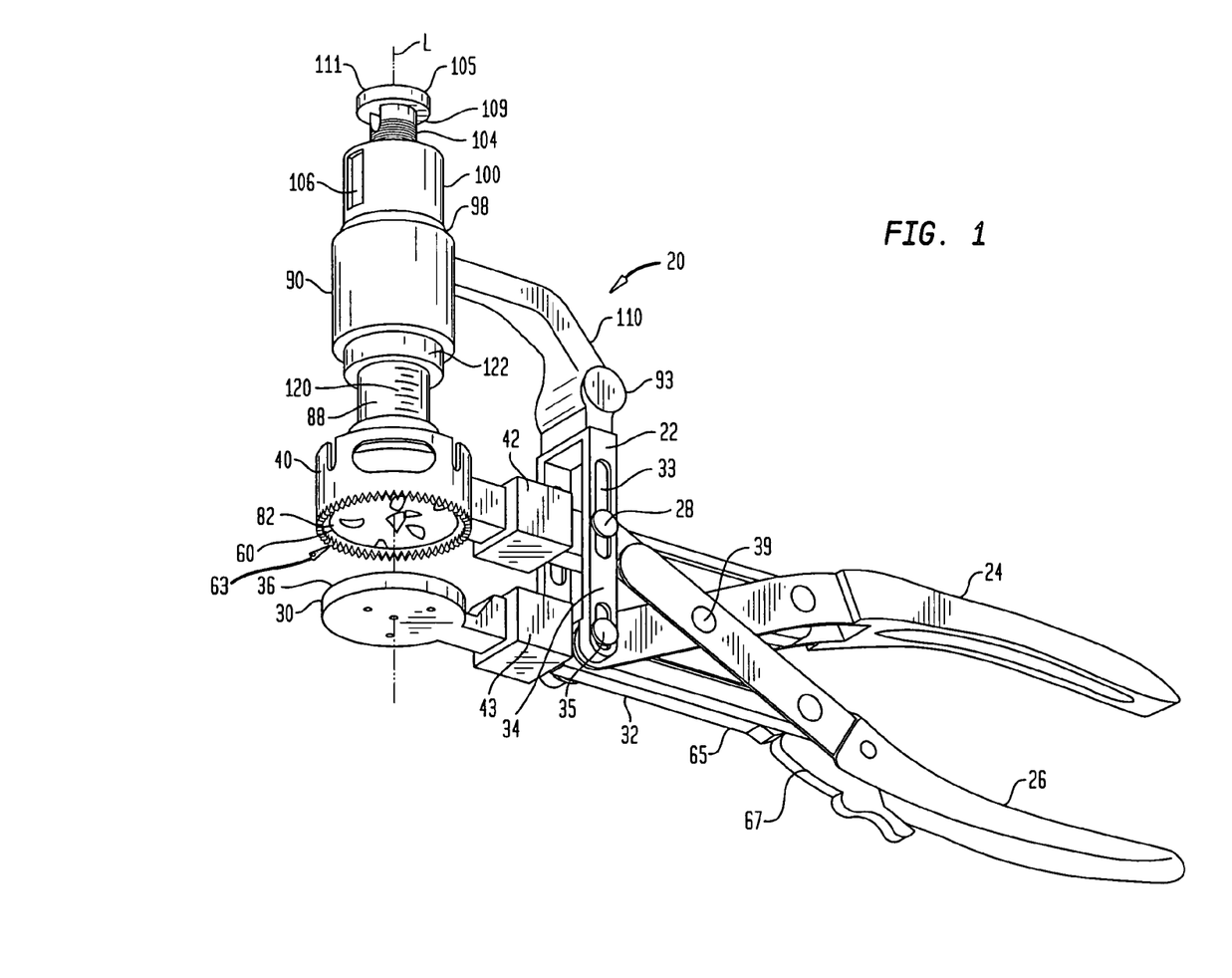
FIG. 1 is an isometric view of the patella clamp of the present invention including the reaming system for milling the posterior face of the patella.

Referring now to the drawings, and especially to FIG. 1 thereof, an apparatus constructed in accordance with the present invention is shown in the form of a patella clamp 20 having a frame 22. An upper arm handle 24 is affixed to the frame 22 and a lower arm handle 26 is mounted upon the frame 22 at pin 28 for sliding movement in a slot 33 of frame 22 toward and away from the upper handle 24. A support platform 30 is attached to frame 22 at a lower end 32 of a side bar 34 of the frame 22. Preferably, platform 30 is removably attached to a carrier 43 which in turn is fixed to side bar 34. A pin 35 mounts arm 24 to frame 22. Platform 30 includes a bone contacting reference surface 36 extending laterally across the upper surface of platform 30. Side bar 34 also include slot 33 in which pin 28 slides. In the preferred embodiment, a patella clamping member shown in the form of a barrel or tubular shaped clamp member 40. Clamp 40 is attached to lower arm 26 by a modular carrier 42 mounted for movement within slot 33 of side bar 34 via pin 28. Clamp 40 is coupled with the lower handle 26 so that pivotal movement of the lower handle 26 with respect to arm 24 about pin 39 will move the carrier 42 longitudinally along the side bar 34 of frame 22 toward and away from platform 30.

Figure 3:
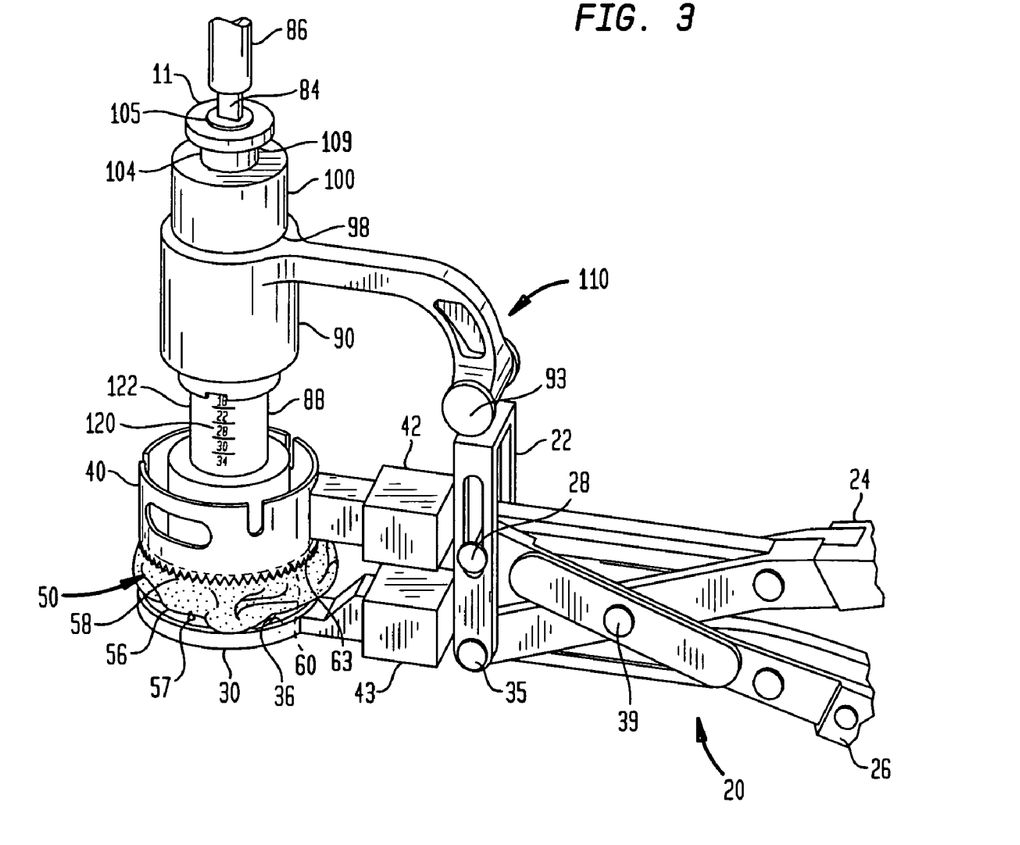
FIG. 3 is an isometric elevation view of the patella clamp of FIG. 1 including the reaming system with a patella mounted therein.

As best seen in FIG. 3, the posterior side of a patella 50 which is to be prepared for the reception of a patellar prosthesis (not shown), is held in a preparation position within the patella clamp 20 by clamp 40 and platform 30. This is done by everting patella 50 and applying patella clamp 20 to the everted patella, with the handles 24 and 26 essentially perpendicular to the mechanical axis of the leg. Alternatively, the patella may be retracted by rotating it less 180° and the clamp 20 applied. Patella 50 includes an anterior surface 56, which contacts surface 36 of platform 30 and a posterior surface 58 facing clamp 40. The patella 50 has a bone thickness extending between anterior surface 56 and posterior surface 58. The posterior surface 58 provides the articular surface of patella 50 and is to be prepared for the reception of a patellar prosthesis. In the preferred construction, bone contacting surface 36 of the reference platform 30 includes spikes 57 to contact and positively locate the anterior surface 56 of the patella 50. Clamp 40 includes teeth 63 around the bone contacting rim 60 and is dramatically sized to extend around the bony periphery of the patellar.

Figure 2:
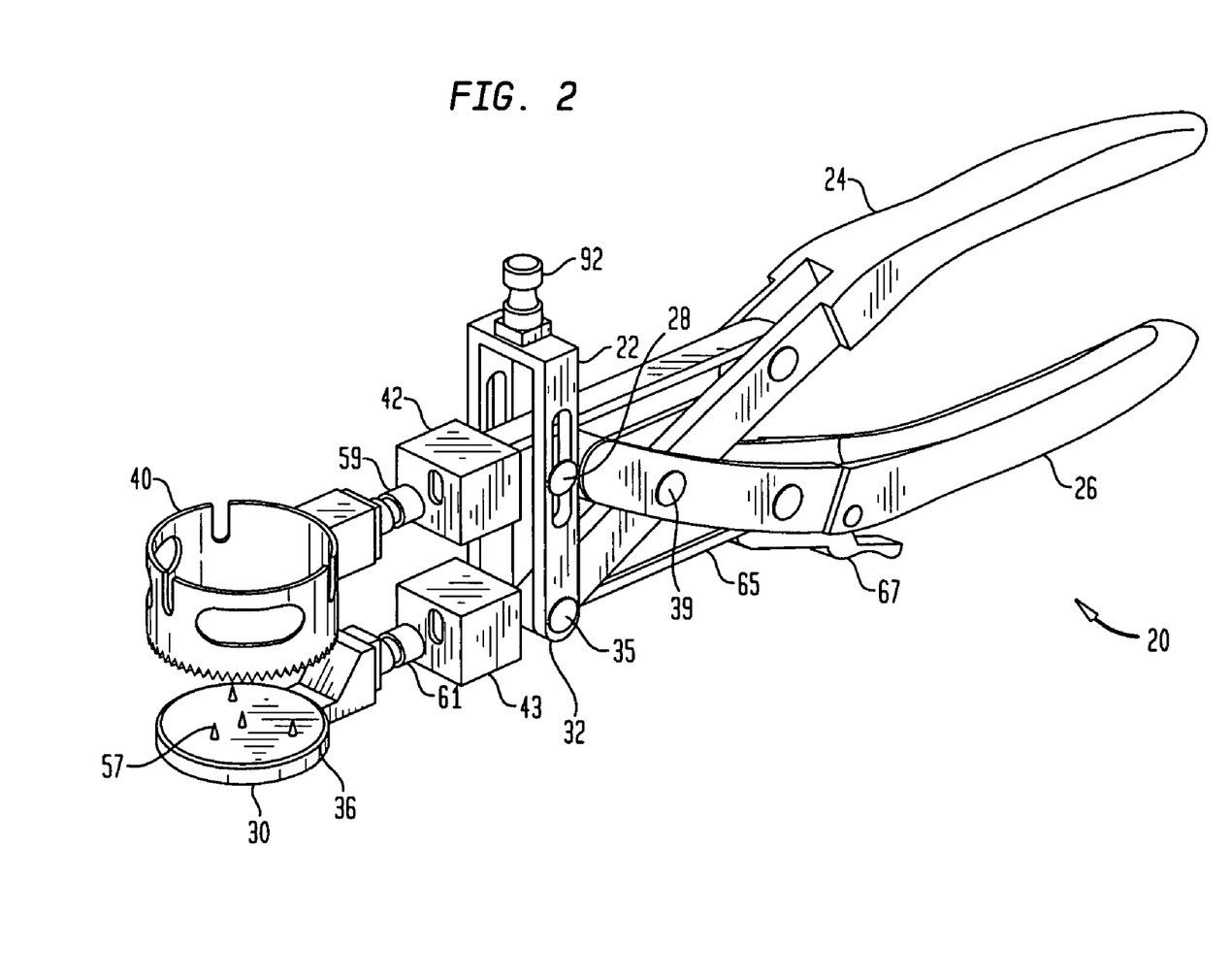
FIG. 2 is an isometric view of the patella clamp of FIG. 1 minus the reaming system.

In the preferred embodiment, as shown in FIG. 2, the clamp member 40 is modular and is removably coupled to carrier 42 of arm 26 by a snap connection 59. Likewise, platform 30 is preferably removably coupled to carrier 43 of arm 24 by a snap connection 61. Thus, two or more clamp members 40 of different size can be used. When the clamp 40 is selected from a plurality of clamp members of different size, the appropriate size is chosen so that arcuate rim 60 of clamp barrel 40 fits closely around the perimeter of patella 50 while resting upon the peripheral bone of patella 50. Preferably, rim 60 includes a plurality of serrated teeth 63 to hold the patella in position during milling. While only two carriers 42, 43 are shown, additional carriers could be mounted on arms 24, 26 if it was desired to include additional modular instruments on clamp 20.

Clamp 20 is applied to patella 50 by moving clamp member 40 toward reference platform 30 until the bone of patella 50 is engaged with patella 50 centrally positioned within rim 60 of clamp member 40. At this point, the patella clamp 20 is secured in place by locking the lower handle 26 against movement away from the upper handle 24, as by a locking ratchet system with ratchet teeth 65 engaged by a trigger lock 67. Alternatively, as shown in U.S. Pat. No. 5,941,884, a lock on one arm can engage a toothed locking rod mounted to the other arm. In this design, a reliable lock button is selectively actuated to release the lock to permit relative movement of the arms and to lock the arms in the selected location by engaging the lock rod.

Figure 4:
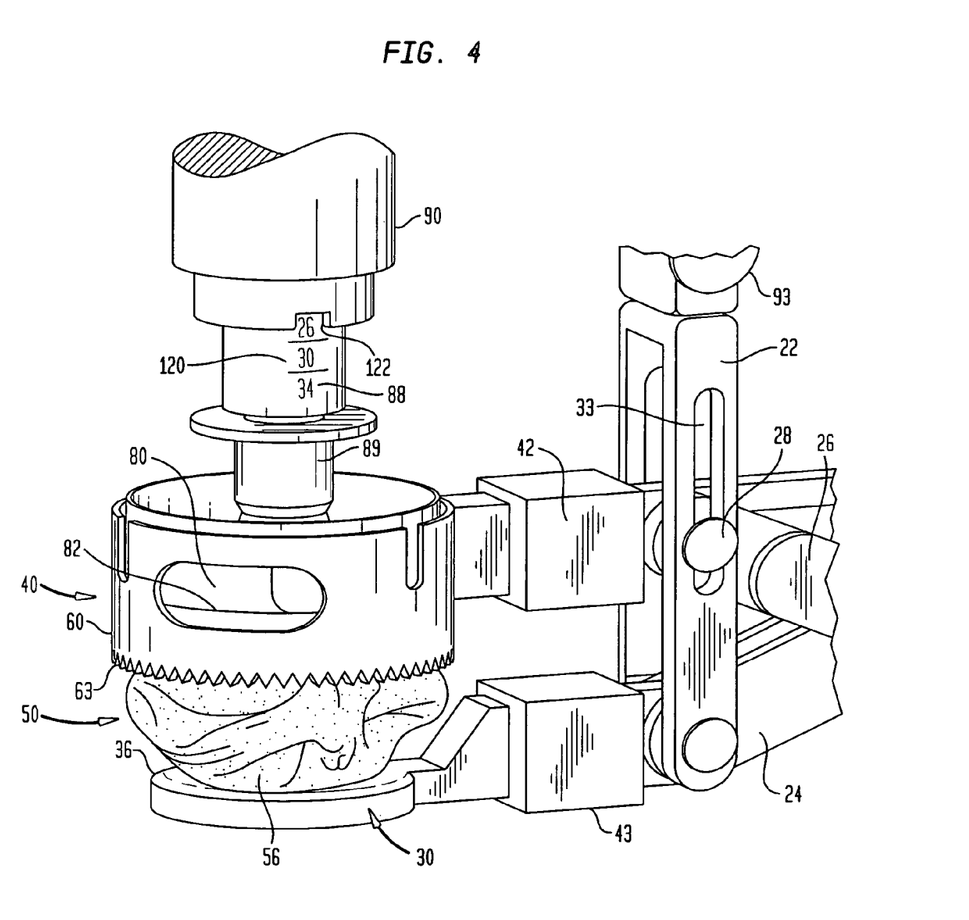
FIG. 4 is an enlarged isometric view of the patella clamp of FIG. 3.
Figure 7:
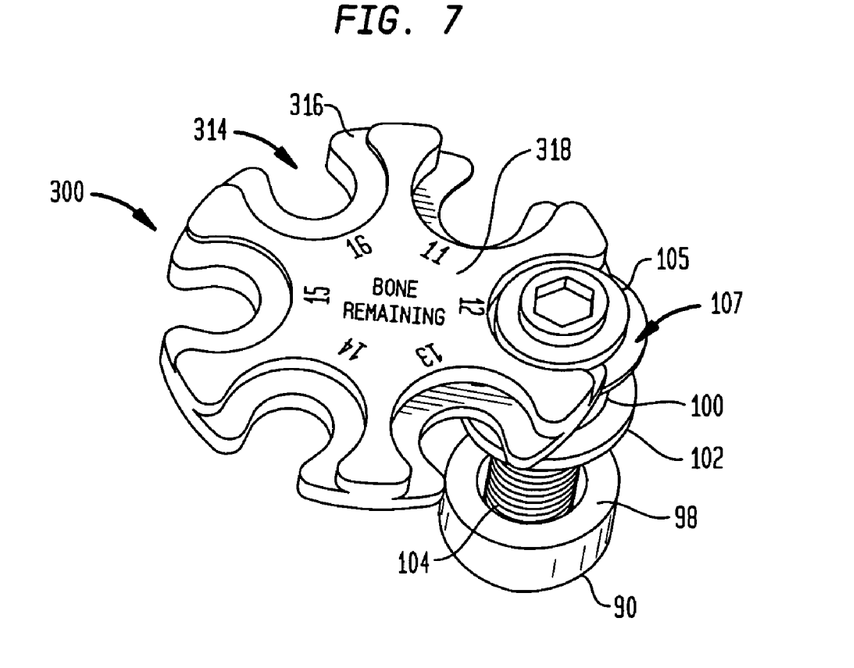
FIG. 7 is an isometric view of the outermost portion of the reaming system of the present invention including a bone remaining depth gage.

Turning now to FIGS. 3 and 4, a bone-cutting tool is employed in the resection of patella 50, and is shown in the form of a reamer or end mill 80 having a rotary cutting face 82 which engages posterior patella face 58, and a shaft 88 for rotating end mill 80. In the preferred embodiment, end mill 80 is releasably attached to shaft 88 by connector 89. Thus end mills of different size can be attached to shaft 88 as desired. Shaft 88 is driven by a modular adapter 84 which includes a drive socket 86 adapted to engage a standard power tool such as a drill (not shown). Preferably, shaft 88 is journaled for rotation in a bushing member 90, about a central longitudinal axis L of the bushing member 90. Shaft 88 is free to move linearly within the bushing member 90 in a direction along the longitudinal axis L. A first stop surface 98 extends laterally along the upper end of the bushing member 90. As best seen in FIG. 7, a stop member in the form of a stop collar 100 includes a second stop surface 102 juxtaposed with and confronting the first stop surface 98. Collar 100 can be adjusted along toothed portion 104 shaft 88. Preferably, collar 100 is releasably engaged with toothed portion 104 at the upper end of the reamer shaft 88. The stop collar 100 is coupled to the toothed portion 104 of shaft 88 by a coupler which includes an actuator button 106 selectively operated to release the stop collar 100. Stop collar 100 moves longitudinally along the toothed portion 104 and button 106 is used to selectively lock the stop collar 100 at a selected location along the toothed extension 104, for purposes to be described hereinafter. In the preferred embodiment, button 106 has internal teeth (not shown) which selectively engage tooth portion 104 to selectively permit movement of collar 100. Toothed portion 104 terminates at a flange 105. Flange 105 may include a socket 107 for receiving modular drive adapter 84. In the preferred embodiment flange 105, toothed portion 104 and the lower portion of shaft 88 are made of one piece. The markings shown may be etched on the lower portion.

In the preferred embodiment, reamer 80, reamer shaft 88, collar 100 and bushing member 90 together comprise an outrigger cutting assembly 110 which is affixed to frame 22 via an attachment 92 as shown in FIG. 2. Attachment 92 is integral with frame 22. A releasable connection including a pin 93 is coupled to assembly 110 so that assembly 110 may be releasably coupled to frame 22 of the patella clamp 20 via attachment 92. This connection locates the bushing member 90 accurately in position relative to the platform 30 reference surface 36 with the axis L intersecting the reference platform surface 36 generally perpendicular to and at the approximate center of the patella preparation position. Thus, the longitudinal axis L is the axis of rotation of shaft 88 and reamer 80 as well as the center of clamp 40.

Once the outrigger cutting assembly 110 is secured to frame 22 of patella clamp 20, as illustrated in FIGS. 1 to 4, the reamer 80 is allowed to drop downwardly, with the reamer shaft 88, until the cutting surface 82 of the reamer 80 rests upon the posterior surface 58 of the patella 50, as shown in FIG. 4. At this point in the procedure, the surgeon is able to determine the thickness of the patella 50 merely by observing an indicator in the form of a visible scale 120 on shaft 88 at the top of recess 122 on the bushing member 90. Thus, as best seen in FIG. 4, as well as in FIG. 3, recess 122 is located accurately relative to platform 30, reference surface 36 and scale 120 is calibrated in terms of distance between cutting surface 82 of reamer 80 and reference surface 36 on which anterior surface 56 of patella 50 rests. In this manner, the surgeon is provided with a quick and accurate direct intra-operative measurement which the surgeon will use to determine the amount of bone to be removed during subsequent resection of patella 50, without the necessity for introducing supplementary instruments or interruption of the procedure.

Once the surgeon determines the amount of bone to be removed during resection, the depth of resection is selected readily, again intra-operatively, directly and without the necessity for supplemental instruments or other apparatus. As discussed below, the surgeon may set the amount of bone to be removed based either on the desired amount of bone the surgeon wants remaining or the amount the surgeon wants to remove. Referring now to FIGS. 3 and 7-9, the longitudinal distance between the first reference surface 98 and the second reference surface 102 determines the extent of longitudinal travel of the reamer 80 as the reamer 80 resects the bone of patella 50. Thus, by setting position of the stop collar 100 on the toothed portion 104, the depth of resection is determined. The toothed configuration of portion 104 assures that the stop collar 100 is moved in precisely determined fixed longitudinal increments related to prescribed increments in the depth of resection. Typically, the increments are provided with a magnitude of one millimeter.

Figure 8:
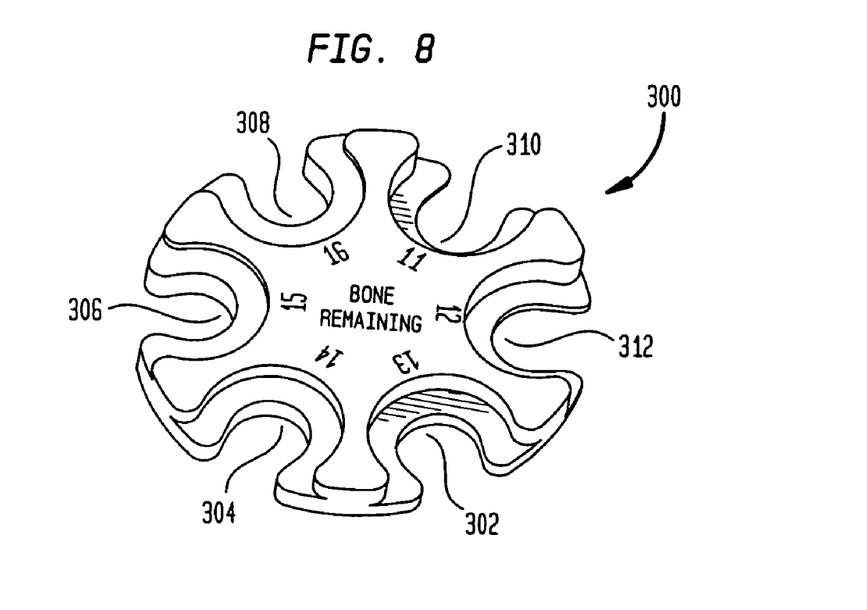
FIG. 8 is an isometric view of the depth gage shown in FIG. 7.
Figure 9:
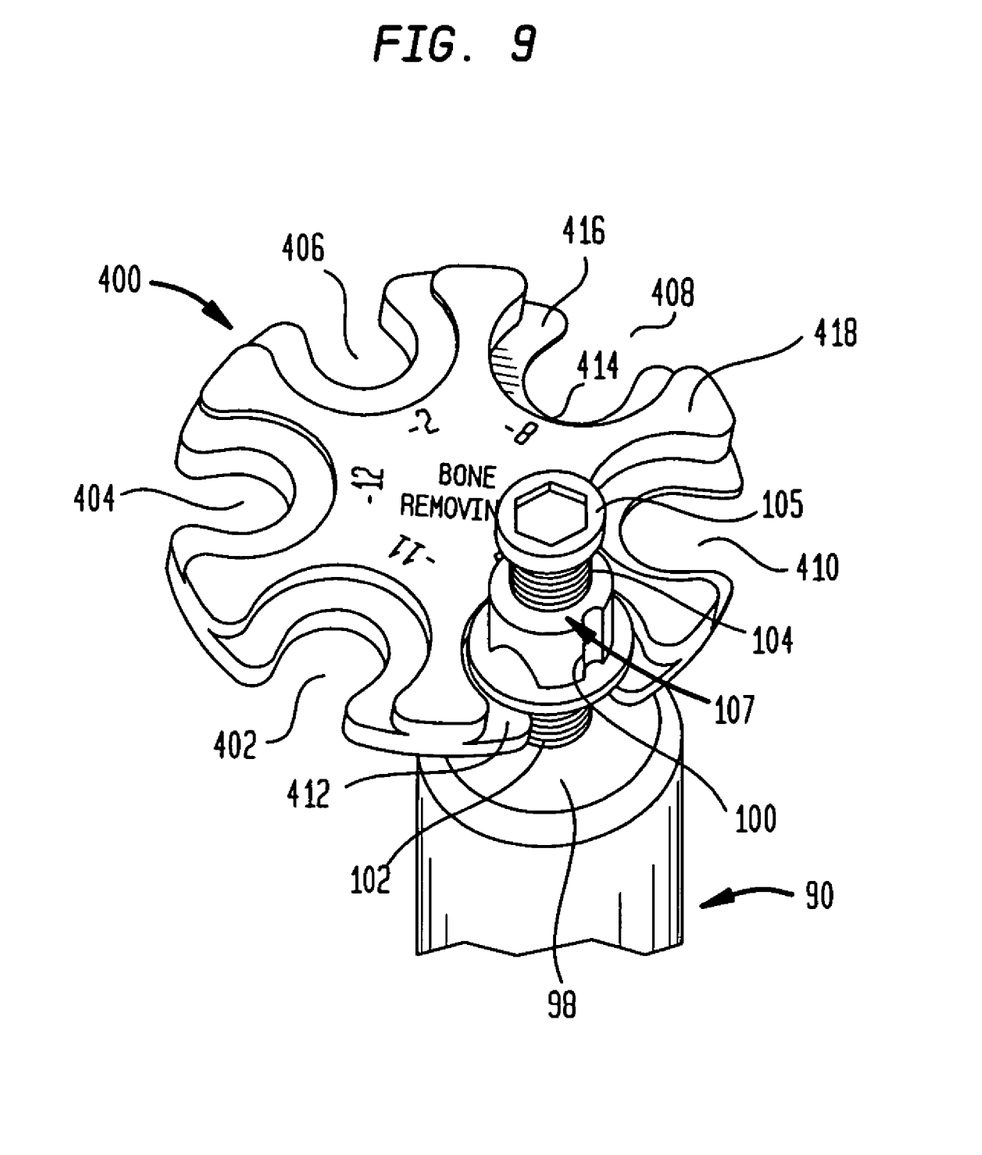
FIG. 9 is an isometric view of the outermost portion of the patella cutting system including a bone removing depth gage capable of setting the amount of bone removed from the patella.

As seen in FIGS. 7-9, the depth of resection may be set in two ways. First, as shown in FIGS. 7 and 8, a depth gage 300 may be used to set the amount of bone remaining. Depth gage 300 includes, in the preferred embodiment, six separate depth gage elements 302-312 which set the amount of bone remaining on patella 50 after engagement of surface 102 and surface 98. In the preferred embodiment, depth gage elements 302-312 start at a minimum of 11 millimeters and increase to 16 millimeters in 1 millimeter increments. Thus, the thickness of the bone remaining may be varied between 11 and 16 millimeters. The bone remaining is set by adjusting the difference between upper surface 107 of stop collar 100 and the bottom of surface 109 of flange 105. This requires that when surface 109 of flange 105 abuts surface 107 of collar 100 and surface 102 then contacts top surface 98 of bushing 90, cutting face 82 is flush with surface 36 of platform 30.

In the preferred embodiment, each gage element 302-312 is in the form of a U-shaped recess 314 surrounded by a surface 316 recessed from top surface 318. The distance between surface 316 and top surface 318 of gage 300 varies to produce a thickness between the bottom surface and the surface 316 equal to the 11 to 16 millimeter desired bone remaining on patella 50. Alternately, the amount of bone removed can be set with a gage 400 which is in all respects similar to gage 300 (i.e., preferably includes six (6) gage elements 402-412) with the exception that to set the bone removing amount, the gage is inserted between surface 98 and surface 102 of stop collar 100. In the preferred embodiment, gage 400 has the identical U-shaped recesses, however, the distance between recessed surfaces 416 and top surfaces 418 are varied to indicate the distance of travel between surface 98 and surface 102 during reaming and indicating how much bone is removed. This is indicated on the top surface of the gage with the six (6) U-shaped openings varying from −7 millimeters to −12 millimeters.

The surgical method of the present invention will now be described. After exposing the patella in a standard manner, the surgeon measures the patella thickness using any one of a number of suitable instruments. Typical ranges of patella thickness as measured between the anterior and posterior surfaces of the natural patella vary from 8 to 40 millimeters and from 30 to 55 millimeters in diameter. Referring to FIG. 2, the surgeon selects a properly sized barrel shaped clamp member 40 and attaches it to carrier 42 which carrier is moveable in slot 33 of side bar 34 by the actuation of handles 24 and 26. Platform 30 is then attached via modular connection 61 to carrier 43 which carrier is stationary with respect to side bar 34 and carrier 42. As indicated above, a plurality of different size clamping barrels 40 may be used so that the periphery of various size patellas may be engaged. In the preferred embodiment, five (5) clamping barrel sizes from 34 millimeters to 50 millimeters in 4 millimeter increments are included in a kit. The teeth 63 of barrel 40 are designed to engage the patella and not the surrounding ligaments. As seen in FIG. 2, a ratcheting mechanism 65, 67 is provided so the surgeon can lock the relative position of carriers 42 and 43 once the patella is firmly clamped as discussed below.

The surgeon now assembles the reaming or milling assembly 110 by choosing a resurfacing patella cutter which matches the clamping barrel 40 size. The assembled cutting assembly 110 is then assembled to frame 22 by means of a connection 92, 93. In the preferred embodiment, the lock is obtained when an audible click is heard, i.e. pin 93 engages extension 92 on frame 22. Of course, any connection The assembled patella clamp is then applied to the everted or retracted patella 50 with the handles 24, 26 with axis L preferably perpendicular to the long axis of the leg. As stated above, the teeth 63 of barrel 40 are moved by the movement of arms 24, 26 towards one another into engagement with the peripheral bone of the patella 50. The ratchet mechanism 65, 67 may be then utilized to lock the clamp in position. Reamer or end mill 82 is then moved into position contacting the posterior surface 58 of patella 50. The current patella thickness is shown on scale 120 as best seen in FIG. 4. The surgeon then has two choices for determining the amount of bone to resect from the patella articulating surface. He may either decide to use the bone remaining method as shown in FIGS. 7 and 8 or the bone removing shown in FIG. 9. As indicated above with regard to gages 300 and 400, there are preferably 6 different bone remaining or bone removing options. With regard to gage 300 the 6 options are 11 millimeters to 16 millimeters in 1 millimeter increments. The utilization of gage 300 as shown in FIG. 7 will determine how much bone the surgeon wishes to remain on the patella. Bone gage 300 is placed on shaft 104 in contact with upper surface 111 of stop collar 100. U-shaped opening 314 must sit flush with reamer shaft 111 and must be placed top flange 105 and top surface 107 of collar 100. Of course, depth gage 300 must be removed prior to milling.

The surgeon also may wish to set the resection level based on the amount of bone removed. In this situation, a gage 400, as shown in FIG. 9, is utilized in a similar manner to gage 300 with the exception that it is located between surface 98 of bushing 90 and bottom surface 102 of stop collar 100. In the preferred embodiment, the six (6) depth removing gage portions include six (6) different bone removing options, −2 millimeters and −8 millimeters to −12 millimeters in 1 millimeter increments. The bone removing depth gage 400 is designed so there can never be less than 10 millimeters left of bone. Again, the U-shaped portion 414 must sit flush around reamer shaft 104 to ensure that the proper depth is set.

Figure 6:
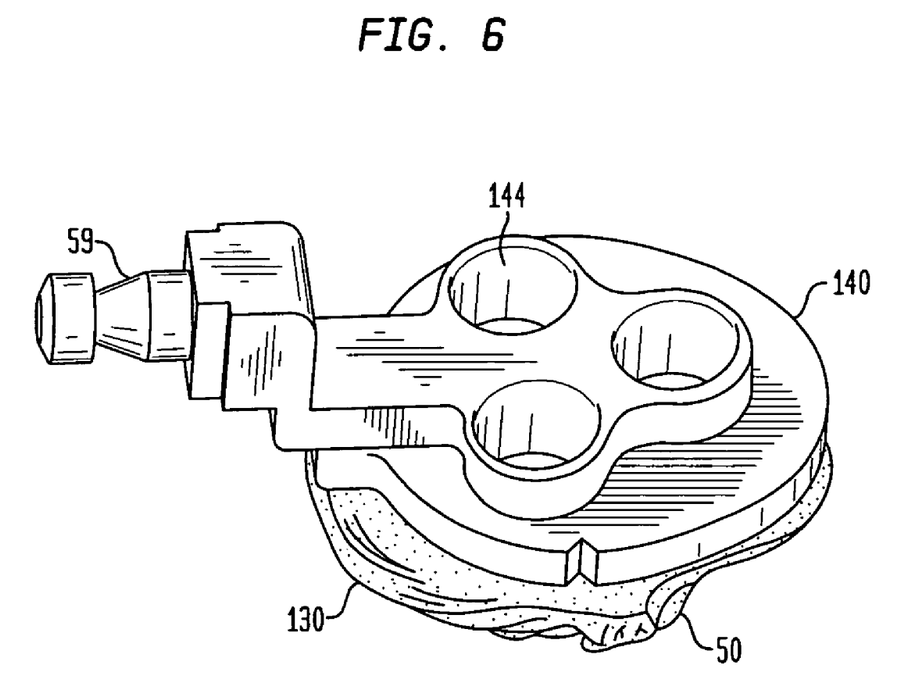
FIG. 6 is an isometric view of the drill guide template disengaged from the patella clamp of FIG. 5.

Once the depth has been set by locating collar 100 based on either the desired bone remaining or the desired bone to be removed, the drive 84, 86 is coupled to recess 107 in flange 105 and the reaming operation is commenced. Reamer 80 is simultaneously rotated and advanced. The reamer shaft is advanced until surface 102 of collar 100 contacts surface 98 of bushing 90. The remaining thickness of the resected patella 50 may then be read from scale 120 on shaft 88. Should the surgeon determine that further resection is required, the stop collar 100 is merely reset to the desired further amount of resection and the reamer 80 then is advanced through the corresponding further amount of linear travel. Once reaming is complete, the surgeon unlocks the ratchet lock using trigger mechanism 65, 67 and releases pin 93 so that the outrigger assembly 110 may be removed thereby exposing the newly created resected surface 130 of the resected patella 50 as shown in FIG. 6. Resected surface 130 is essentially planar and normal to axis L.

Figure 5:
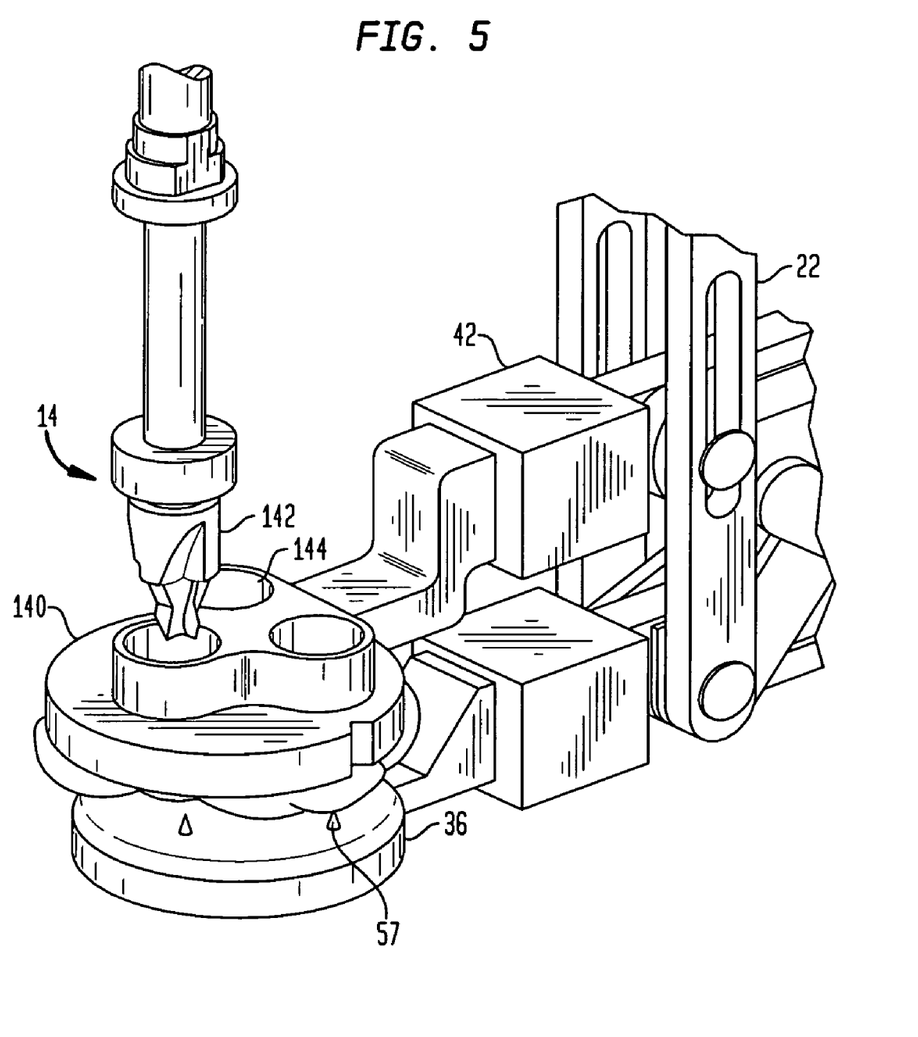
FIG. 5 is an isometric view of the patella clamp of FIG. 1 including a modular drill guide template mounted thereon.
Figure 11:
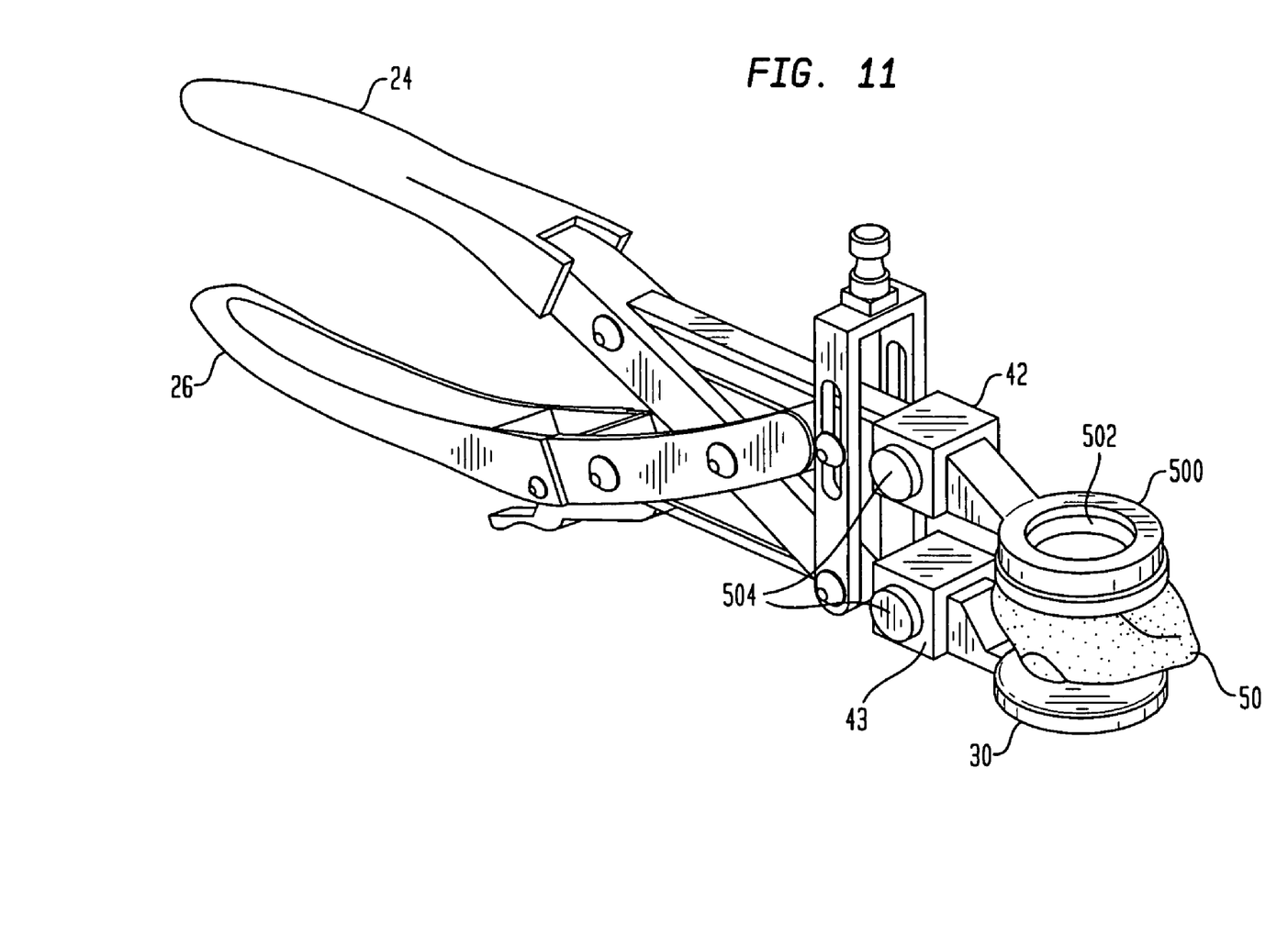
FIG. 11 is an isometric view of the patellar clamp of the present invention including a modular clamp for engaging the posterior surface of a polyethylene patella implant.

Referring to FIGS. 5 and 6, fixation hole placement can be done in a well known manner utilizing the drill template 140 and the drill assembly 141. To accomplish this, barrel clamp 40 is removed from carrier 42 and the template 140 which includes a connector 59, is inserted into place in carrier 42. Again, in the preferred embodiment, there is a series of drill templates for various size prosthetic patellas with the template chosen providing the most complete coverage of the resurface patella without any overhang. With patella clamp 20 secured in place so that the drill template 140 is located in position against resected surface 130, as illustrated in FIGS. 5 and 6, an assembly 141 including drill 142 is advanced through the apertures 144 in the drill template 140 for appropriate location of holes in patella surface 130. These holes correspond to the lugs of a typical patellar prosthesis (not shown). As is well known, a trial prosthesis may be placed on surface 130 of the resected patella 50 and the overall anterior/posterior thickness may be measured to determine whether the proper patella thickness has been restored. The patella tracking can then be assessed prior to the permanent implantation of the prosthetic patella implant. Normally, the prosthetic patella is made of polyethylene and a clamping element shown in FIG. 11 may be provided for attachment to arm 26 and used in a manner similar to barrel clamp 40 and drill template 140. Referring to FIG. 11 there is shown a clamp part 500 for pressing on the posterior side of the patellar implant 502 while clamp platform 30 presses on the anterior bony portion of the patella. This clamping can be performed during the curing of bone cement holding the polyethylene implant to the prepared patella surface. Also shown in FIG. 11 are release buttons 504 which are used to disengage the various clamping elements from carriers 42, 43.

Thus, after forming the holes, template 140 would be removed and a modular clamp shaped to receive the posterior surface of the polyethylene implant would be mounted on connector 42. The activation of handles 24, 26 then applies pressure on the implant forcing, in the preferred embodiment, the three lugs on the implant into the three drilled holes. The implant may be either press fit or cemented into place on the remaining bone of the patella. If cementing is used, the clamp 20 may be utilized to maintain pressure while the cement cures (see FIG. 11).

Figure 10:
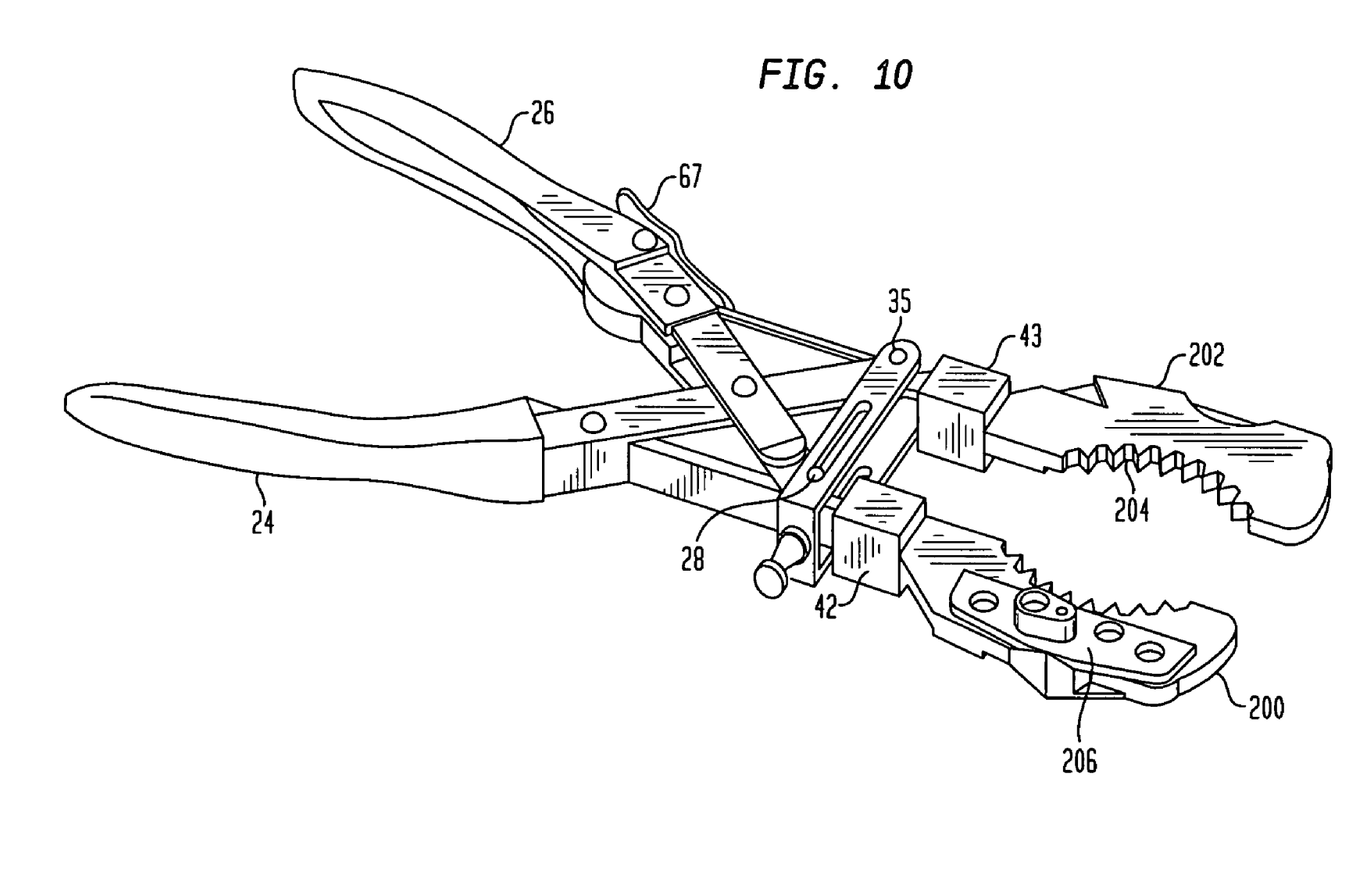
FIG. 10 is an alternate embodiment of the patella clamp in which a pair of jaw members intended to grip the periphery of the patella are provided.

Referring to FIG. 10 there is shown an alternate embodiment of the patella clamp of the present invention. The body of the clamp including handles 24, 26, frame 22, carriers 42, 43 remains the same. However, instead of platform 30 and barrel shaped clamping member 40, a pair of arms 200, 202 are provided with connection portions similar to 59 and 61. Thus, prior to insertion of plate 30 and member 40 or after the removal of plate 30 and barrel member 40, arms 200, 202 are snapped into position in carriers 42, 43. Arms 200, 202 have bone engaging teeth 204 designed to engage the periphery of the patella. The clamp can now grip the periphery of a patella. A saw guide 206 can be attached to either or both arms 200, 202 for guiding a saw blade (not shown). Thus, after arms 200, 202 securely grip patella 50, the posterior surface thereof may be resected in a known manner. Arms 200, 202 of different size can be provided and may be provided as part of a kit which may include all or some of the clamp 20, two or more platforms 30 and clamp elements 40 of different size, gages 300, 400, and two or more clamps 500 and two or more cutters 80.

In the preferred embodiment, buttons 304 have recesses designed to receive and lockingly engage elements 59, 61. Buttons 504 are spring loaded so that when the buttons are released they lock onto pins 59, 61. Depressing buttons 504 then releases the pins 59, 61 so that the modular instruments/clamping elements may be removed. A similar system is used to releasably mount assembly 110 to pin 92 via button 93.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patellar resurfacing clamp comprising:
a first part having a first surface engageable with a surface of the patella and including a second surface spaced from said first surface;
a second part moveable with respect to the first part along a first axis;
a patella cutting element coupled to said first part and moveable with respect to said first part along the first axis, said cutting element having a shaft the shaft having an end flange having a stop surface spaced from the first part first surface along the first axis through the shaft and an adjustable collar mounted on the shaft for movement with respect to the first axis of the shaft between the first part second surface and the flange stop surface, said adjustable collar on said shaft having a first stop surface engageable with said second surface on said first part for spacing said cutting element a distance from said first part first surface and the adjustable collar having a second surface spaced from the collar first stop surface axially along the shaft; and
at least one movable gage element moveable in a direction perpendicular to the first axis insertable between either the first stop collar surface to set the distance between said first stop surface on the adjustable collar and said second surface of said first part or insertable between the flange stop surface and the collar second surface for selectively setting the position of said adjustable collar on said shaft with respect to the first surface contacting the patella based on either the amount of patella bone being removed or the amount of patella remaining.

2. The patella clamp as set forth in claim 1 wherein there are two gage elements moveable in a direction perpendicular to the first axis, one insertable between the first part second surface and the collar first stop surface for setting the position of said collar along the shaft with respect to said amount of bone removed and one insertable between the collar second surface and the flange stop surface for setting the position of said collar along the shaft with respect to the amount of bone remaining.

3. The patellar clamp as set forth in claim 1 wherein the shaft is a drive shaft.

4. The patellar clamp as set forth in claim 3 wherein said shaft has a portion having external teeth for engaging the collar.

5. The patellar clamp as set forth in claim 4 wherein said collar has an internal locking element for selectively engaging said external teeth on said shaft to set the adjustment of said collar along said first axis.

6. The patellar clamp as set forth in claim 5 wherein said collar is moveable from a first position where said collar may slide along the first axis with respect to said shaft to a second position where said teeth on said shaft and said collar engage and prevent further axial movement.

7. The patellar clamp as set forth in claim 1 further comprising a second part movable along the first axis with respect to the first part, the second part includes a tubular clamping jaw for engaging a surface of the patella opposite a patella surface engaging said first surface of said first part.

8. The patellar clamp as set forth in claim 7 wherein said tubular clamping jaw acts as a guide for said cutting element.

9. The patellar clamp as set forth in claim 8 wherein said tubular clamping jaw is removably attached to said second part so that a size of said jaw may be varied by providing a plurality of clamping jaws of different diameters.

10. The patellar clamp as set forth in claim 7 wherein said clamping jaw includes teeth for engaging the patella bone.

11. The patellar clamp as set forth in claim 2 further comprising a scale on the shaft indicating a posterior-anterior thickness of said patella, the scale independent of the moveable gage element.

12. The patellar clamp as set forth in claim 1 wherein said cutting element is an end mill.

13. The patella clamp as set forth in claim 1 wherein said cutting element is a reamer.

14. The patellar clamp as set forth in claim 1 wherein upon engagement of said shaft flange stop surface and the second surface on said collar said collar first stop surface is spaced from said first part second stop surface a distance along the first axis allowing a cutting face of said patella cutting element to contact said first surface of said first part when said collar first stop surface and said first part second surface contact.

15. The patellar clamp as set forth in claim 14 wherein the distance between said collar second surface and said shaft flange stop surface along said first axis is equal to the bone remaining on the patella after cutting the patellar by moving said cutting element until said collar first stop surface engages said second surface of said first part.

16. The patellar clamp as set forth in claim 15 wherein said at least one movable gage element has a plurality of steps of different height for varying the bone remaining thickness on the patella by spacing the second surface of the collar a desired distance along the first axis corresponding to one of the different heights from said flange stop surface.

17. The patellar clamp as set forth in claim 16 wherein the distance along the first axis between said collar first stop surface and said first part second surface is equal to the bone to be removed from the patella.

18. The patella clamp as set forth in claim 17 wherein said at least one gage has a plurality of steps of different height for varying the amount of patella bone removed by spacing the collar first stop surface a desired distance along the first axis from said first part second surface.

19. A patella clamping system comprising:
a first clamp part having a reference surface engageable with an anterior surface of a patella, said first part including a stop surface spaced from said reference surface along a first axis;
a cutting element for resecting bone from a patella, the cutting element rotatably mounted on said first clamp part and moveable with respect to said axis, said cutting element having a first adjustable stop surface engageable with said stop surface on said first clamp part and a second non-adjustable stop surface spaced from the first adjustable stop surface;

a first movable gage element insertable between said first adjustable stop surface on the cutting element and said stop surface on said first clamp part by movement in a direction generally perpendicular to the first axis for setting the position of said adjustable stop surface with respect to the reference surface on said first clamp based on the amount of bone to be removed from the patella; and a second movable gage element insertable between the second non-adjustable stop surface and a second adjustable surface on the cutting element by movement in a direction generally perpendicular to the first axis for setting the position of said first adjustable stop surface with respect to the reference surface on said first clamp based on the amount of bone to remain on the patella.

20. The patellar clamp as set forth in claim 19 wherein said cutting element includes a shaft extending along the first axis having the non-adjustable stop surface capable of engaging the second adjustable stop surface on said cutting element and upon engagement of said surfaces, said first adjustable stop surface on said cutting element is spaced from said first part stop surface a distance allowing a cutting face of said cutting element to be positioned adjacent said reference surface of said first part when said adjustable first stop surface and said first clamp part stop surface contact.

21. The patellar clamp as set forth in claim 20 wherein the distance between said second adjustable stop surface and said shaft non-adjustable stop surface along said first axis is equal to the bone remaining on the patella after cutting the patella by moving said cutting element until said first adjustable stop surface engages said stop surface of said first clamp part.

22. The patellar clamp as set forth in claim 21 wherein the first gage element has a plurality of steps of different height for varying the bone remaining thickness on the patella by spacing the second adjustable stop surface a desired distance along the first axis from said non-adjustable stop surface on said shaft upon insertion between the non-adjustable cutting element stop surface and the second adjustable stop surface.

23. The patellar clamp as set forth in claim 22 wherein the distance along the first axis between said first adjustable cutting element stop surface and said first clamp part stop surface is equal to the bone to be removed from the patella.

24. The patella clamp as set forth in claim 23 wherein said at least one gage has a plurality of steps of different height for varying the amount of patella bone removed by spacing the first adjustable stop surface a desired distance along the first axis from said first clamp part stop surface upon insertion between the first adjustable cutting element stop surface and the first clamp part stop surface.

* * * * *